US006830567B2

(12) United States Patent
Schuele et al.

(10) Patent No.: US 6,830,567 B2
(45) Date of Patent: Dec. 14, 2004

(54) METHOD AND DEVICE FOR NON-INVASIVE REGULATION OF TEMPERATURE WITH RADIATION, ESPECIALLY LASER RADIATION OF BIOLOGICAL TISSUE

(75) Inventors: Georg Schuele, Luebeck (DE); Ralf Brinkmann, Luebeck (DE)

(73) Assignee: Medizinisches Laserzentraum Luebeck GmbH, Luebeck (DE)

( * ) Notice: Subject to any disclaimer, the term of this patent is extended or adjusted under 35 U.S.C. 154(b) by 154 days.

(21) Appl. No.: 10/201,250

(22) Filed: Jul. 24, 2002

(65) Prior Publication Data

US 2003/0032949 A1 Feb. 13, 2003

(30) Foreign Application Priority Data

Jul. 24, 2001 (DE) .......................................... 101 35 944

(51) Int. Cl.[7] .................................................. A61F 9/007
(52) U.S. Cl. ............................... 606/4; 128/898; 374/17
(58) Field of Search .............................. 606/4, 27, 28, 606/5; 374/17; 600/402–405; 128/898

(56) References Cited

U.S. PATENT DOCUMENTS

| 5,657,760 A | * | 8/1997 | Ying et al. .................. 600/439 |
| 5,830,139 A | * | 11/1998 | Abreu ......................... 600/405 |
| 5,876,121 A | * | 3/1999 | Burns et al. ................ 374/161 |
| 6,012,840 A | * | 1/2000 | Small et al. ................ 374/126 |
| 6,381,025 B1 | * | 4/2002 | Bornhop et al. ............ 356/517 |

* cited by examiner

Primary Examiner—Roy D. Gibson
Assistant Examiner—Henry M Johnson, III
(74) Attorney, Agent, or Firm—Crowell & Moring LLP (57) ABSTRACT

A method and a system for the non-invasive temperature determination on biological tissue, particularly at the fundus of the eye, treated by a treatment radiation, particularly laser radiation, wherein, during the respective irradiation time, at essentially identical time intervals, additional radiation pulses of a shorter pulse duration and a lower energy are aimed at the treated biological tissue, the resulting tissue expansions and/or contractions being detected by a pressure measurement or optical measurement and, from the measuring signals, the absolute temperature values are determined and optionally the treatment radiation is controlled as a function thereof.

17 Claims, 9 Drawing Sheets

METHOD AND DEVICE FOR NON-INVASIVE REGULATION OF TEMPERATURE WITH RADIATION, ESPECIALLY LASER RADIATION OF BIOLOGICAL TISSUE

The invention relates to a method and to a system for the non-invasive determination of the temperature on biological tissue treated by means of radiation, particularly laser radiation.

It is known to determine the tissue temperature in the thermal treatment of biological tissue by means of optoacoustic techniques (K. V. Larin, I. V. Larina, M. Motamedi, R. O. Esenaliev, "Monitoring Temperature Distribution with an Optoacoustic Technique in Real Time", SPIE Proc. 3916: 311–321, 2000).

It is known from German Patent Document DE 199 32 477 A1 to determine by means of optoacoustic techniques material changes caused on biological tissue by pulsed irradiation.

From G. Schüle, G. Hüttmann, J. Roider, C. Wirbelauer, R. Birngruber, R. Brinkmann, "Optoacoustic Measurement during µs-Irradiation of the Retinal Pigment Epithelium, SPIE Proc. Vol. 3914: 213–236, 200, it is known to measure the temperatures at the treated ocular fundus during the selective microphoto coagulation at the ocular fundus for the treatment of diseases of the retina by means of µs laser pulses. The pressure amplitude caused by the first treatment pulse was used for standardizing the pressure amplitude to the temperature of the ocular fundus. From the pressure amplitude increase of the subsequent treatment pulses, the temperature increase and, in addition, the respective absolute temperatures were determined by means of the dependence of the temperature on the pressure amplitudes known from calibration measurements.

In many spheres of ophthalmology, different energy sources, particularly lasers, are used for diagnostics and treatment. As a rule, the entire beamed-in energy is absorbed by the biological tissue and converted to heat, the resulting temperature increase achieving the desired treatment effect. For example, during laser photocoagulation, the retina of the eye is thermally coagulated in a targeted manner. In the case of the conventional irradiations with irradiation times about 100 ms, temperatures occur of above 60° C. Also, in the case of transpupillary thermotherapy (TTT), temperatures increases are utilized for achieving a vascular occlusion. In the case of photodynamic therapy (PDT), a previously injected dye is activated by laser irradiation on the ocular fundus. The active ingredient develops its effect only on those cells to which to which it is bound. In this case also, almost the entire beamed-in energy is absorbed in the dye and in the retina and is converted to heat. During the respective irradiation time (pulse duration) with relatively long treatment and radiation pulses in the order of from µs to several hundred seconds, a temperature increase of the treated biological tissue, particularly of the fundus of the eye, may occur which results in unintended damage to regions of the retina. A non-invasive real-time temperature determination could not yet be carried out in eye treatments of this type.

SUMMARY OF THE INVENTION

It is therefore an object of the invention to provide a method and a system for the non-invasive determination of the temperature on treated biological tissue, particularly in ophthalmology, in which radiation pulses are used for the treatment radiation.

With respect to the method, this object is achieved according to the invention by means of the characteristics of claim 1 and, with respect to the system, the object is achieved by means of the characteristics of claims 8 and 9.

According to the invention, during the respective irradiation period of the treatment radiation, additional radiation pulses of a shorter pulse duration and a lower energy than during the treatment radiation are aimed at the treated biological tissue, or the treatment radiation is switched off for a short time and is switched back on again. The additional radiation pulses or the short-duration switch-offs of the treatment radiation may take place essentially at the same time intervals. The thermal tissue expansions occurring when the additional radiation pulses are used and the tissue contractions occurring during the short-duration switch-offs of the treatment radiation are detected by a pressure measurement or by an optical measurement. From the respective measuring signals, which are caused by the additional radiation pulses (measuring radiation pulses) or the short-duration switch-offs of the treatment radiation, the temperature increase is determined; particularly the respective absolute values of the temperature are determined.

In the case of the invention, the pulse energy of the additionally beamed-in radiation pulses or the switch-off time, during which the treatment radiation is switched off several times, will be constant. The energy applied into the tissue causes a temperature-dependent, optoacoustically analyzable, thermal expansion of the tissue, for which the green iron coefficient is a measurement. By means of calibration measurements, a calibration curve is obtained which has a linear rise of the acoustic amplitudes with the temperature according to the green iron coefficient (G. Schüle, G. Hüttmann, J. Roider, C. Wirbelauer, R. Birngruber, R. Brinkmann, "Optoacoustic Measurement during µs Irradiation of the Retinal Pigment Epithelium, SPIE, Proc., Vol. 3914: 230–236, 2000).

In the case of the invention, short-duration laser pulses are preferably used with a few ns, for example 8 ns, and with a low pulse energy of a few µJ, for example 5 µJ. The laser pulses may also be longer. Because of the high light absorption at the fundus of the eye, particularly of the retinal pigmentary epithelium (RPE), the low pulse energies are sufficient for obtaining sufficient measuring values, particularly of the pressure measurement (acoustic measurement) and of the optical measurement. In the case of the pressure measurement, preferably a maximal value or an integral of the respectively measured pressure half-wave is used for the analysis during the temperature determination. However, other algorithms, such as the slope or a Fourier transformation of the measuring signals, can also be used in the analysis.

As an optical measurement, an interference measurement by means of an interferometer is preferably used, particularly a fiber interferometer whose measuring beam is coupled into the treatment lens system of the treatment radiation.

Preferably, during the switch-on of the treatment radiation by means of an additional short-duration radiation pulse or immediately after the switch-on of the treatment radiation by means of a short-duration switch-off, a measuring signal is obtained from the occurring tissue expansion or contraction, which measuring signal is standardized to the normal body temperature, for example, the human body temperature of 37° C.

On the basis of the continuous monitoring of the temperature also during the respective irradiation time (pulse duration) of the treatment radiation, a control of the treatment radiation can be carried out as a function of the respective determined temperature at the irradiation site. In this case, particularly the pulse duration or pulse power of the treatment beam can be controlled in order to obtain the desired temperature at the irradiation site.

BRIEF DESCRIPTION OF THE DRAWINGS

These and other objects, features and advantages of the present invention will become more readily apparent from the following detailed description of currently preferred configurations thereof when taken in conjunction with the accompanying drawings wherein.

DETAILED DESCRIPTION OF THE DRAWINGS

Figure 1:
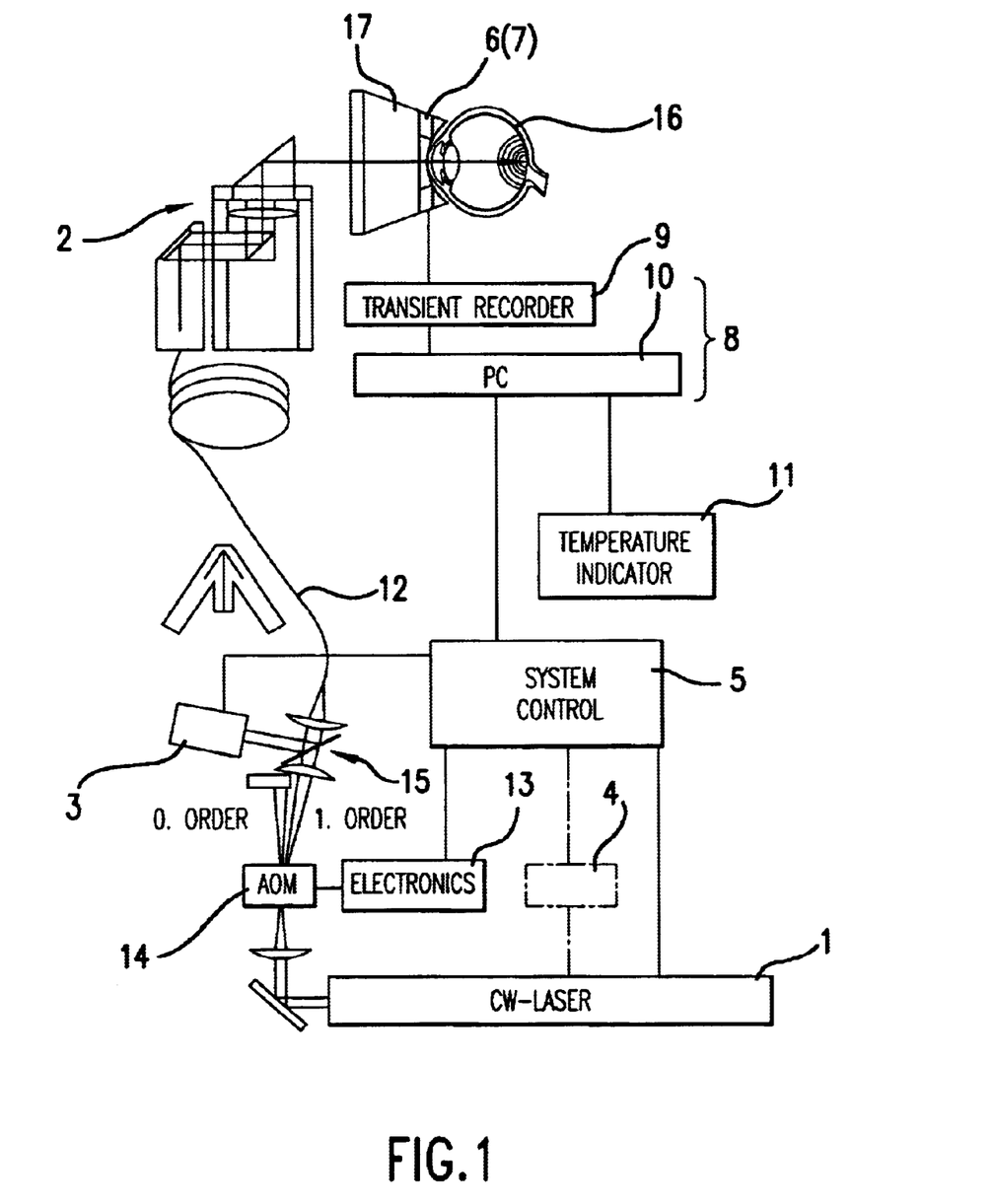
FIG. 1 is a view of a first embodiment for a system for implementing the invention.
Figure 2:
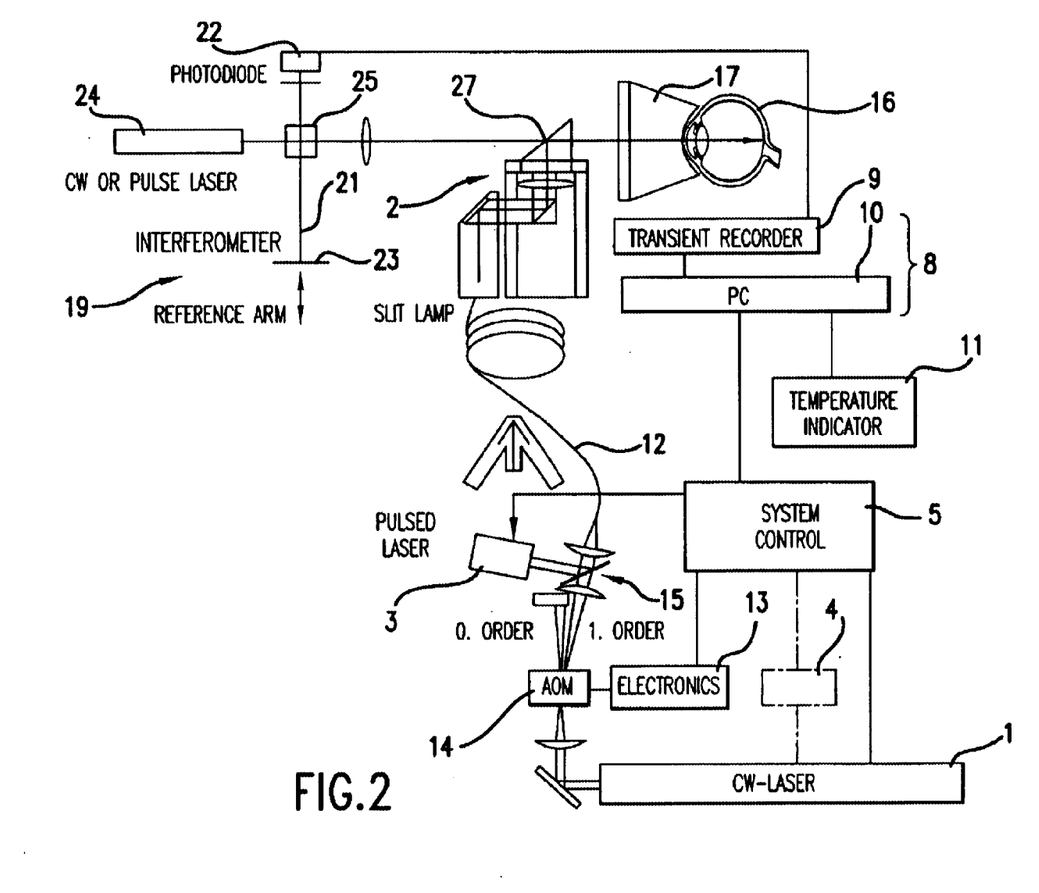
FIG. 2 is a view of a second embodiment of a system by means of which the invention can be implemented.
Figure 3:
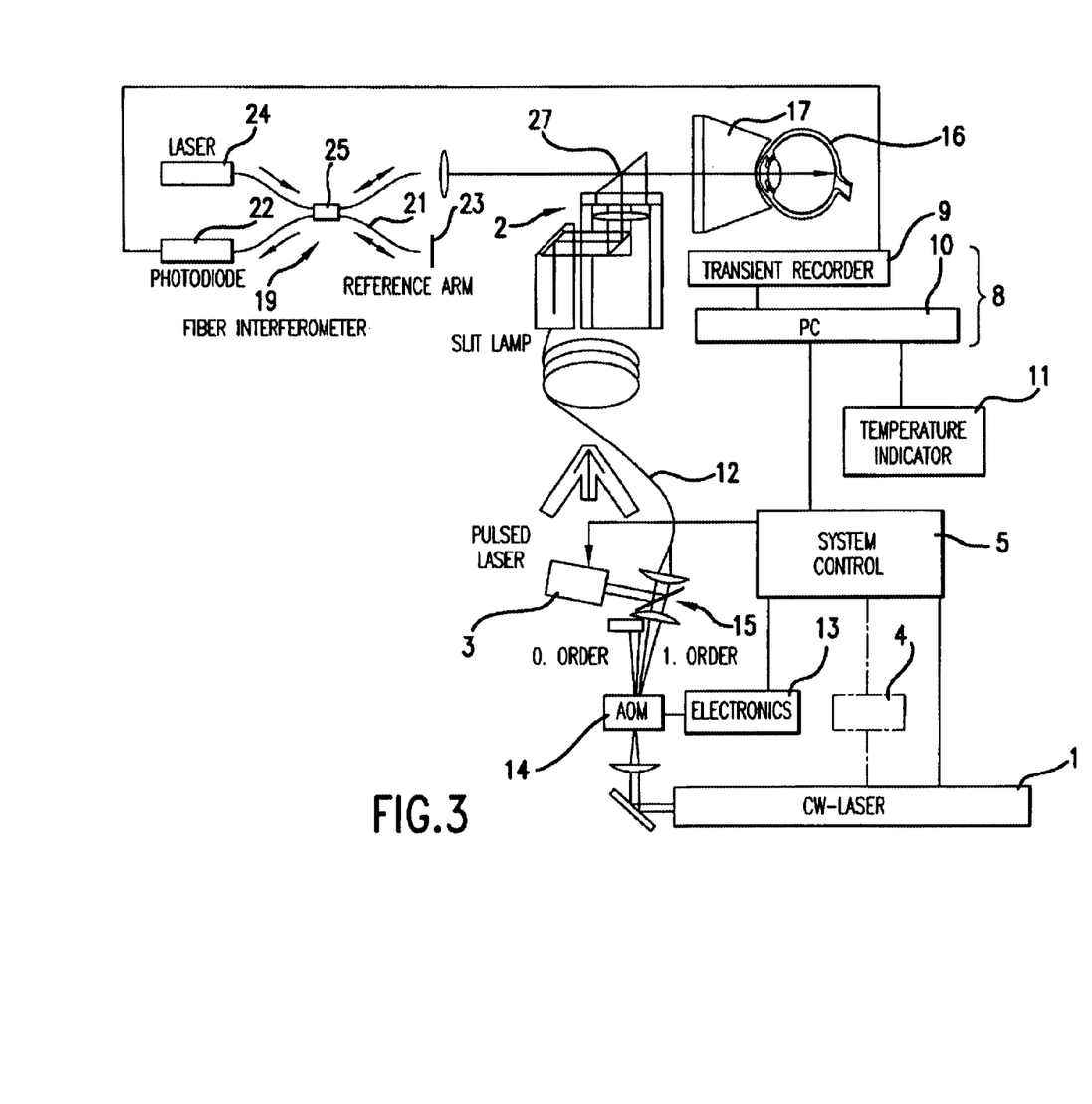
FIG. 3 is a view of a third embodiment.

The system illustrated in FIGS. 1 to 3 partially together with a block diagram contains a treatment radiation source, such as a laser beam source, particularly a continuous-wave laser. The treatment radiation source 1 generates the treatment radiation used for the treatment of the ocular fundus. The treatment radiation is processed and, by way of a switch 14 controlled by an assigned electronic control system 13, for example, an acousto-optical modulator, mechanical shutter or the like, and a coupler lens system 15, coupled into an optical waveguide, such as a glass fiber 12. At the glass fiber end, an irradiation lens system 2 is situated, for example, in the form of a slit lamp, by means of which the treatment radiation is aimed at the fundus, particularly the retina of an eye 16.

The treatment radiation source 1 is controlled by a control device 5. By way of the control device 5, particularly the radiation energy and the time duration can be controlled by means of which the treatment radiation can be aimed at the ocular fundus.

Furthermore, the systems illustrated in FIGS. 1 to 3 have an additional radiation source 3 in the form of a pulsed laser. The radiation of the additional radiation source 3 can be coupled by means of a coupler lens system 15, which may have a semi-transmitting mirror, into the beam path of the treatment radiation. In the illustrated embodiments, this coupling-in takes place before the or simultaneously with the coupling-in of the treatment radiation into the optical waveguide 12. The illustrated systems are preferably used in the phototherapy of certain points at the fundus of the eye, particularly of pigmented tissue, for example, in photodynamic therapy (PDT). In this case, a previously injected dye is activated by laser irradiation at the fundus of the eye. For this purpose, laser pulses are used, for example, which have an irradiation time (pulse duration) of approximately 90 seconds. As a rule, in photodynamic therapy, this pulse duration corresponds to the treatment time.

Further, the illustrated systems can be used for the photocoagulation by means of laser radiation as the treatment radiation. The treatment duration is approximately 100 ms. For this purpose, a continuous-wave laser pulse with a corresponding pulse duration is used. Furthermore, a transpupillary thermotherapy (TTT) can be carried out. For this purpose, the irradiation takes place in the second range and a vascular occlusion is achieved resulting from the targeted temperature rise.

In addition, a selective RPE treatment can be carried out. In this case, laser pulses are used as treatment radiation which have a pulse duration of approximately 30 $\mu$s during a treatment time of approximately 300 ms.

By means of the illustrated systems, additional short-duration radiation pulses are superimposed on the radiation pulses of the treatment radiation. The pulse duration of the additional radiation pulses is several hundred times to several thousand times shorter with respect to time than the treatment times (pulse durations) of the treatment radiation. The pulse durations of the additional radiation, particularly of the additional laser pulses, which are generated by the additional radiation source 3, have a pulse duration of several ns, for example 5 to 100 ns. The pulse energy is also extremely low and amounts to several $\mu$J, for example, approximately 5 $\mu$J. The additional radiation pulses coupled at regular intervals by the coupler lens system 15 into the treatment radiation have a constant pulse energy. The additional pulses cause short-duration thermal expansions of the treated biological tissue which can be detected by measuring the pressure (FIG. 1) or by measuring the interference (FIGS. 2 and 3). The amplitudes of these short-duration expansions are proportional to the temperature of the biological medium.

Figure 4:
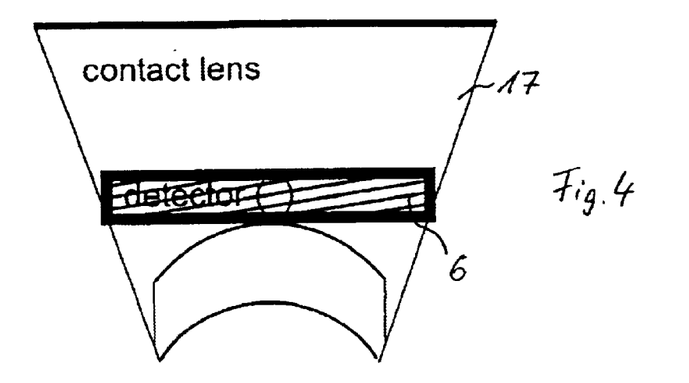
FIGS. 4 to 12 are views of embodiments of detector arrangements for detecting the thermal tissue expansion or contraction.
Figure 5:
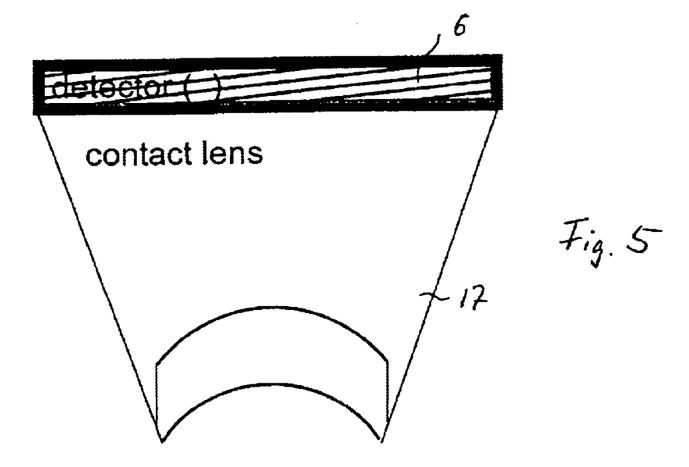
Figure 6:
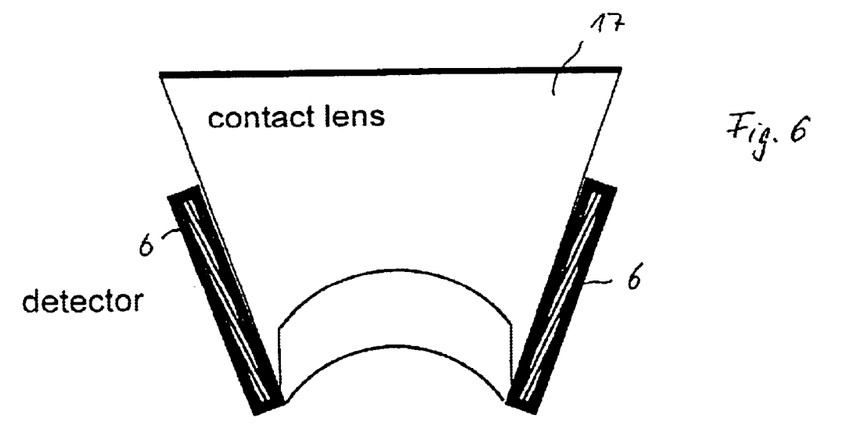
Figure 7:
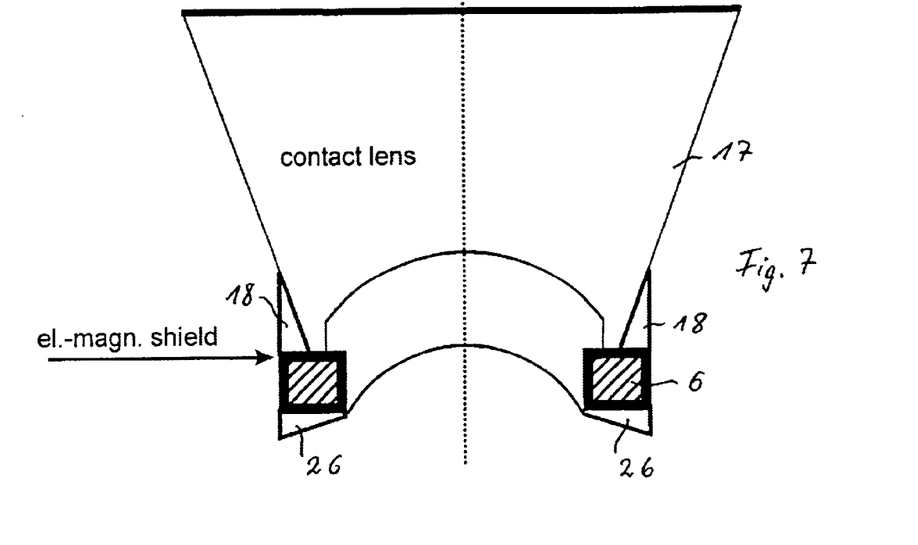
Figure 8:
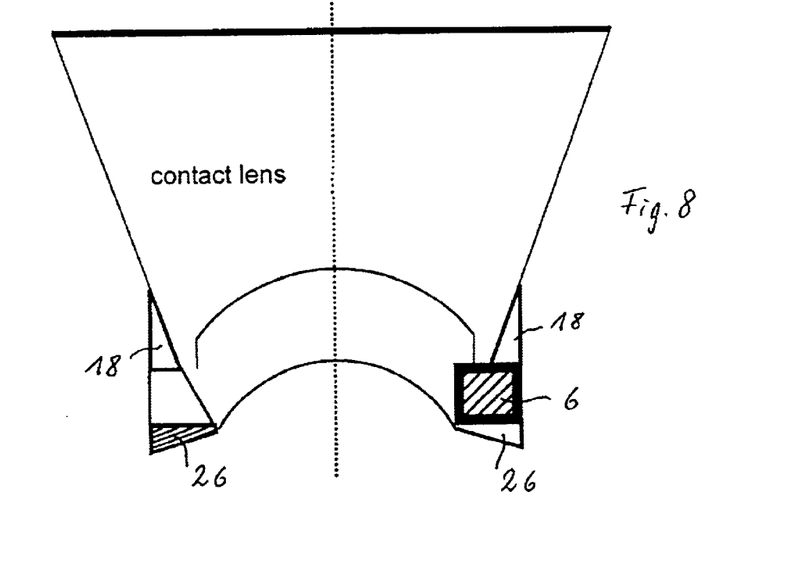

In the embodiment illustrated in FIG. 1, these thermal expansions at the fundus of the eye are detected by an acoustic converter 6 which receives the pressure waves emitted by the tissue expansions and converts them to electrical signals. For this purpose, the acoustic converter 6 is arranged in or on a contact lens 17 which can be placed on the eye and receives the pressure waves by way of the eyeball. Sound detectors of the arrangements illustrated in FIGS. 4, 5 and 6 may be provided as acoustic converters 6. The sound detectors may, for example, consist of a piezoelectric material. In the embodiment illustrated in FIG. 7, a ring-shaped acoustic converter 6 is provided which may also consist of a piezoelectric material. In the embodiment illustrated in FIG. 8, the converter 6 is situated on one side of the contact lens 17.

Figure 9:
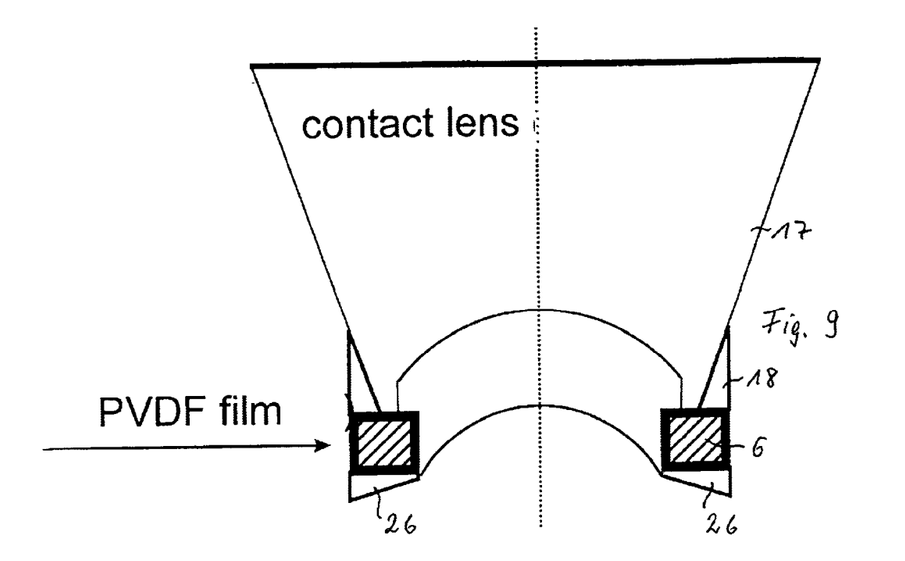
Figure 10:
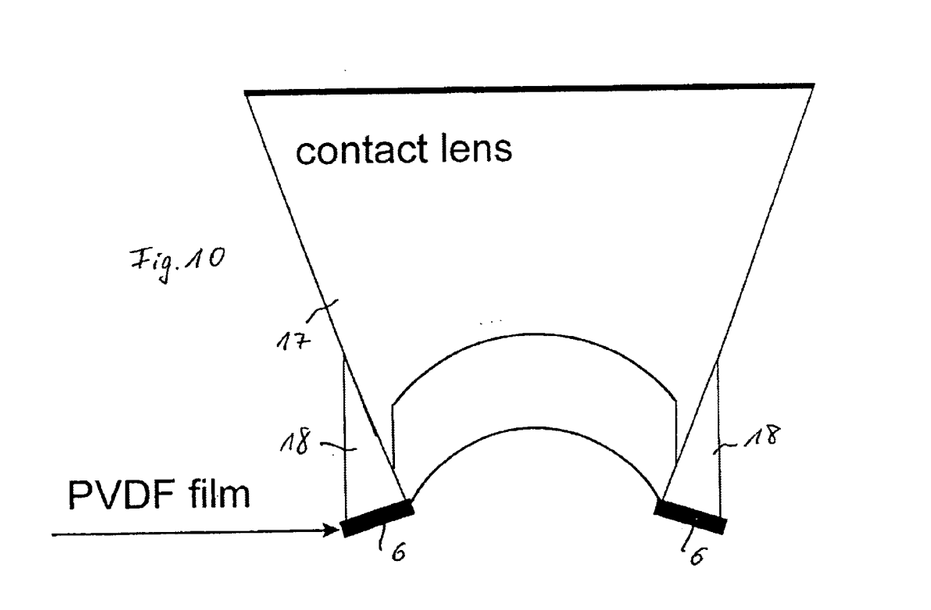
Figure 12:
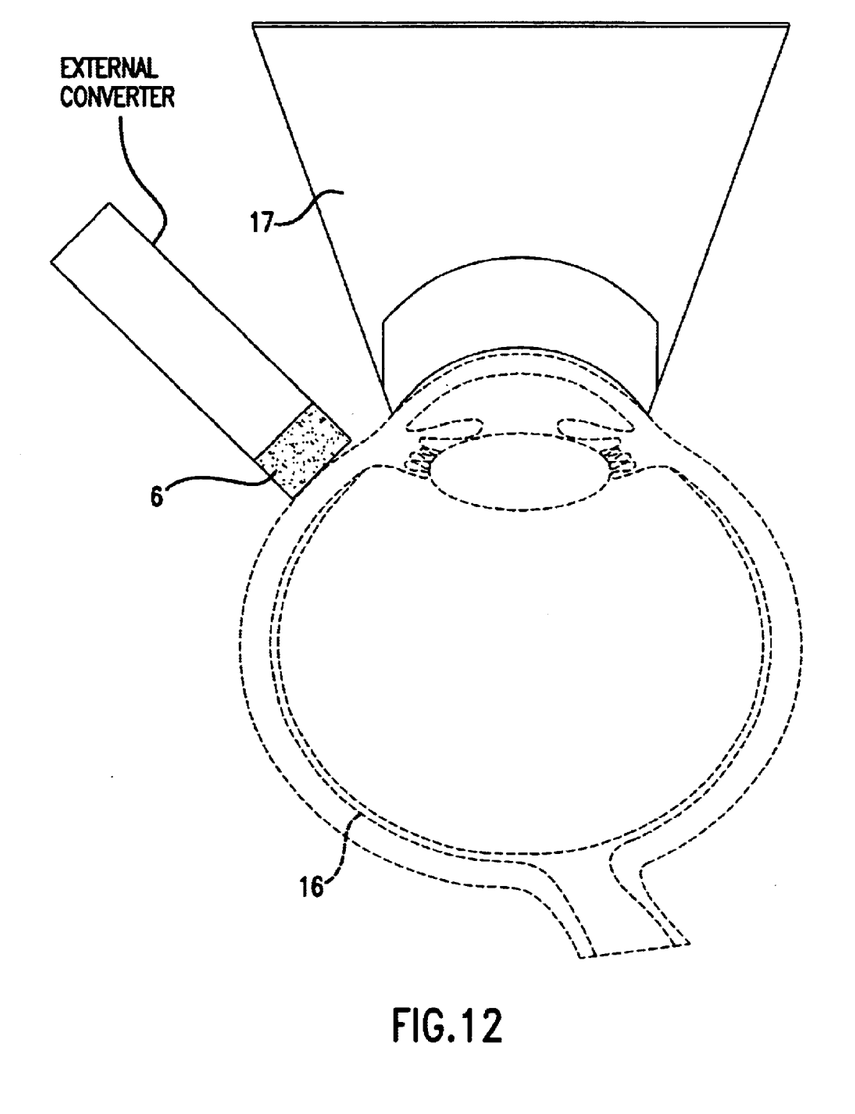

In the embodiments of FIGS. 9 and 10, the acoustic converter 6 consists of polyvinylidene fluoride (PVDF). In the embodiment illustrated in FIG. 10, a PVDF film is provided as a piezoelectric element. On their front side, the acoustic converters 6 illustrated in FIGS. 7 to 10 have an acoustic impedance matching device 26 in the form of a conical placing edge of the contact lens 17 adapted to the eye in order to achieve a better introduction of sound into the converter 6. The sloped contact surface ensures an improved contact with the surface of the eye. On the rearward side, the converters 6 have an acoustically absorbing layer 18 in order to reduce reflections of the sound waves. In the embodiment illustrated in FIG. 12, an external converter 6 is used which can be placed on the eye 16.

Figure 11:
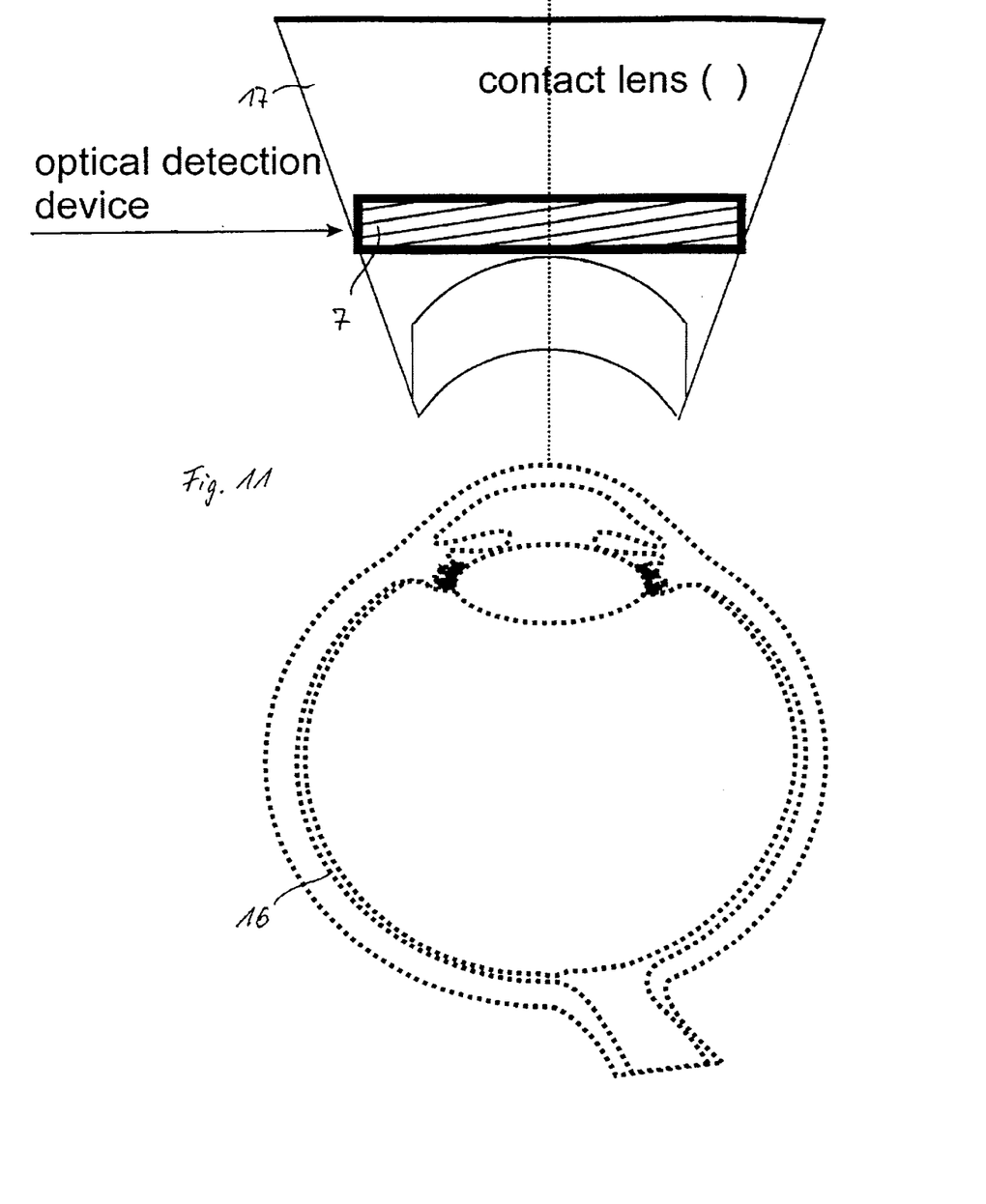

In the embodiment illustrated in FIG. 11, an interferometric detector 7 is installed into the contact lens 17. As a function of the pressure waves on the ocular fundus generated by thermal expansion, the interference phenomena at the detector 7 will change. These can be detected, for example, by way of a photodiode 22, as in the embodiments of FIGS. 2 and 3, and can be analyzed by way of a transient recorder 9 in a computer of an analyzing device 8 with respect to absolute temperature values.

The measuring values of the detectors, which are illustrated in FIGS. 3 to 9, are fed as electrical transients to the transient recorder 9 in FIG. 1 and are converted in the computer 10 to the absolute values of the temperature. The absolute values of the temperature can be indicated by way of a temperature indicating device 11 which is connected to the computer 10.

In the embodiments illustrated in FIGS. 2 and 3, an interferometer 19, which is constructed as a dual-beam interferometer, is used for detecting the thermal tissue expansions. The interferometer 19 of FIG. 3 is constructed as a fiber interferometer. In a known manner, the illustrated interferometer 19 has a radiation source 24 which may be constructed as a cw or pulsed laser. The radiation emitted by the radiation source 24 is introduced in a measuring beam path 20, for example, by way of a beam splitter 27 at the irradiation lens system 2 into the treatment beam path and, at the fundus of the eye, impinges on the site treated by the treatment beam.

In addition, the illustrated interferometer 19 has a reference reflector 23 to which the radiation emitted by the beam source 24 is fed by way of a beam splitter 25 in a reference beam path 21. The reference reflector 23 can be moved for in-stage purposes in the direction of the reference beam path 21. During the treatment and the temperature measurement, the distance from the beam splitter 25 remains constant.

Figure 13:
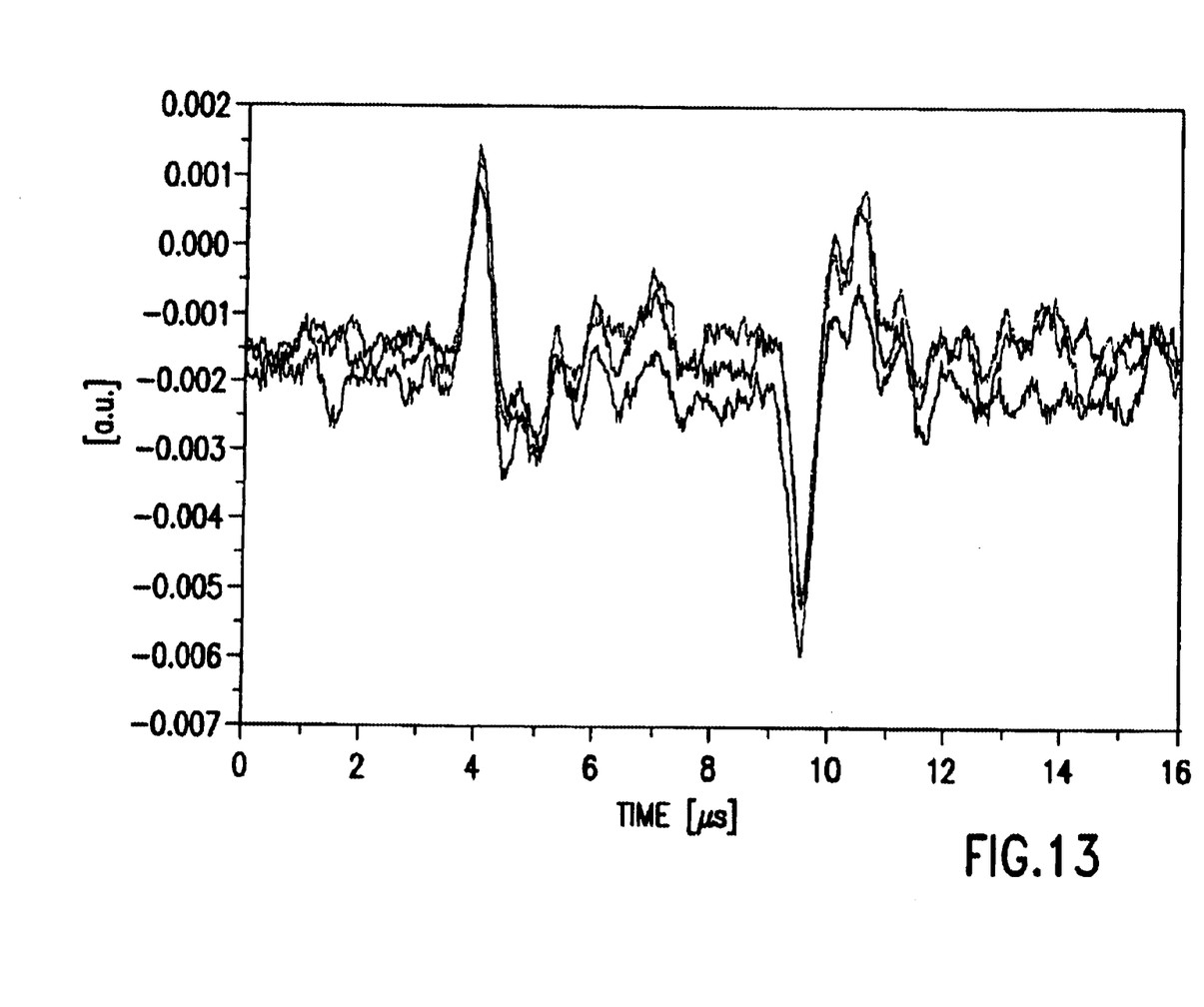
FIG. 13 is a graph of electrical signals which represent optoacoustic transients.

The radiation of the radiation source 24 reflected by the fundus of the eye and the radiation reflected by the reference reflector 23 are guided together at the beam splitter 25 and, as a function of the thermal expansions at the fundus of the eye, interferences occur which are detected by a photodiode 22. The changes or transitions of the reference phenomena are fed to the transient recorder 9 in the form of electrical signals. FIG. 13 illustrates optoacoustic transients which are measured during the switch-on and switch-off of a 5 µs laser pulse applied to the RPE. During the switch-on, a positive pressure wave is obtained as a result of the thermal expansion. During the switch-off, a negative pressure wave (tension wave) is formed by the cooling-down. This amplitude is higher because of the now higher temperature. This corresponds to the absolute temperature increase. In the computer 10 of the analyzing device 8, the temperature values will then be determined therefrom, as in the embodiment of FIG. 1. The absolute values of the temperature can also be indicated by the indicating device 11.

In the two embodiments of FIGS. 1 and 2, the temperature values are fed to the control device 5. As a function of these temperature values, the control or actuation of the treatment radiation source 1 takes place as mentioned above.

The embodiments of FIGS. 1 to 3 were explained in connection with an additional pulsed radiation source 3. This pulsed radiation source 3 can generate, preferably at firmly defined time intervals, the short-duration additional radiation pulses which are coupled by means of the coupler lens system 15 into the beam path of the treatment radiation source 1. It is also possible that the additional radiation source 3 is controlled by the control device 5.

As an alternative to the additional radiation source 3, a switching device 4 may be provided which switches off the treatment radiation source 1 during the respective irradiation time for a short duration (several nanoseconds) and, in the case of a long treatment radiation time, up to several seconds, and switches it on again. As illustrated by a dash-dotted line, for this purpose, the switching device 4 may be correspondingly controlled by the control device 5. During the short-duration switch-off of the treatment radiation, a contraction of the treated tissue takes place at the fundus of the eye, which also causes a pressure wave which can be detected by the above-described detectors (detectors of FIGS. 4 to 12) or the interferometer 19 (FIGS. 2 and 3). The analysis of the thus obtained measuring signals will then take place in the same manner as explained above.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

List of Reference Numbers

1 Treatment radiation source
2 irradiation lens system (such as slit lamp)
3 additional radiation source
4 switching device
5 control device
6 detector (acoustic)
7 detector (optical)
8 analyzing device
9 transient recorder
10 computer
11 temperature indicating device
12 optical waveguide (glass fiber)
13 electronic control system for the acousto-optical modulator
14 switch, such as an acousto-optical modulator
15 coupler lens system
16 eye
17 contact lens
18 acoustically absorbing layer
19 interferometer
20 measuring beam path
21 reference beam path
22 photodiode
23 reference reflector
24 radiation source
25 beam splitter
26 impedance adaptation

What is claimed is:

1. Method for non-invasive determination of temperature on biological tissue, including the fundus of an eye, treated by radiation, comprising during a respective irradiation period by the treatment radiation, aiming additional radiation, which have pulses of a shorter pulse duration and a lower energy than those pulses generated during the treatment radiation at the biological tissue, or switching off the treatment radiation for a short time and switching the treatment radiation back on, detecting resulting at least one of tissue expansions and contractions by one of a pressure or an optical measurement, and from a signal from the measurement, determining at least one of temperature and the temperature rise.

2. Method according to claim 1, wherein, during the optical measurement, the at least one of tissue expansions and contraction is detected by interference measurement.

3. Method according to claim 1, wherein, during the pressure measurement, an electric pressure transient is formed for analysis during the temperature determination.

4. Method according to claim 1, wherein the additional radiation pulses or the short-duration switch-off of the treatment radiation occur at substantially the same time intervals.

5. Method according to claim 1, wherein the treatment radiation is controlled as a function of the determined temperature.

6. Method according to claim 1, further comprising determining a temperature at the fundus of an eye which is treated by radiation.

7. Method according to claim 1, wherein during or immediately after switch-on of the treatment radiation, a measuring signal standardized to normal body temperature is obtained from the resulting tissue expansion or contraction.

8. Method according to claim 1, wherein, based on continuous monitoring of temperature during the respective irradiation period of the treatment radiation, control of the treatment radiation is carried out as a function of the respective determined temperature at an irradiation site.

9. System for non-invasive determination of temperature of biological tissue which is treated by radiation, including laser radiation, with a defined treatment time, comprising a treatment radiation source for generating the treatment radiation, a control device configured to control the treatment radiation source during the defined treatment time, an irradiation lens system for aiming the treatment radiation at the biological tissue, an additional radiation source which, during the treatment time, is coupleable into the irradiation lens system for supplying additional radiation pulses, a detector for measuring by at least one of acoustically and optically at least one of expansions and contractions caused by the radiation, and an analyzing device which has a calibration curve indicating proportionality of the at least one of acoustically and optically detected measuring signals to the temperature and so as to convert the detected measurement into a temperature value.

10. System according to claim 9, wherein the radiation pulses of the additional beam source have a lower energy than the treatment radiation, and pulse duration is less than the respectively defined irradiation time.

11. System according to claim 10, wherein the pulse duration of the additional radiation pulses or a switch-off time of the treatment radiation is smaller by at least a factor of $10^2$ than the respective irradiation time of the treatment radiation.

12. System according to claim 10, wherein the pulse duration of the additional radiation pulses or the switch-off time of the treatment radiation is in the ns range.

13. System according to claim 9, wherein the analyzing device is operatively connected to the control device.

14. System according to claim 9, wherein the analyzing device is operatively connected to a temperature indicating device which indicates absolute temperature values.

15. System according to claim 9, wherein the detector is a measuring converter coupleable acoustically or optically to the human eye.

16. System according to claim 15, wherein the detector is coupleable to the treated eye by a contact lens placeable on the eye.

17. System for non-invasive temperature determination of biological tissue which is treated by radiation, including laser radiation with a defined treatment time, comprising a treatment radiation source for generating the treatment radiation, a control device configured to control the treatment radiation source during the defined treatment time, an irradiation lens system for aiming the treatment radiation at the biological tissue, a switching device operatively controlled by the control device during the respectively defined irradiation time, to switch the treatment radiation source off for a short duration and then back on, a detector for measuring at least one of acoustically and optically at least one of expansions and contractions caused by the radiation, and an analyzing device which has a calibration curve indicating proportionality of the at least one of the acoustically and optically detected measurements to temperature so as to convert the measurement signal into a temperature value.

* * * * *